United States Patent [19]

Wagner

[11] 4,393,870
[45] Jul. 19, 1983

[54] SUCTION INJECTOR

[76] Inventor: Wolfgang Wagner, Exercierstrasse 1, 1 Berlin 65, Fed. Rep. of Germany

[21] Appl. No.: 241,378

[22] Filed: Feb. 26, 1981

Related U.S. Application Data

[60] Continuation-in-part of Ser. No. 93,615, Nov. 9, 1979, Pat. No. 4,284,077, which is a division of Ser. No. 933,136, Aug. 14, 1978, abandoned, which is a continuation-in-part of Ser. No. 793,951, May 5, 1977, Pat. No. 4,114,691, which is a continuation-in-part of Ser. No. 634,741, Nov. 21, 1975, abandoned.

[51] Int. Cl.³ ............................................. A61M 5/00
[52] U.S. Cl. ..................................................... 604/115
[58] Field of Search ............... 128/215, 218 R, 218 A, 128/218 F, 216, 276, 302

[56] References Cited

U.S. PATENT DOCUMENTS

| 1,934,046 | 11/1933 | Demarchi | 128/215 |
| 2,743,723 | 5/1956 | Hein | 128/215 |
| 3,122,138 | 2/1964 | Geary | 128/215 |
| 4,114,619 | 9/1978 | Wagner | 128/215 |
| 4,284,077 | 8/1981 | Wagner | 128/215 |

Primary Examiner—John D. Yasko

[57] ABSTRACT

A suction injector comprises a suction cup and an exchangeable cannula inserted into the cup for injecting a liquid medicine under human skin by the action of a piston movable in a cylinder. The suction cup is formed with an outer chamber which accumulates negative pressure and an inner chamber closed with a membrane which is placed over the skin to be treated. A tubular member is provided in the suction cup having a number of flexible projections adapted to prevent communication of the negative pressure in the outer chamber to the inner chamber until the membrane is in pressure contact with the skin and to break this communication when the membrane with the skin are lifted towards the cannula.

14 Claims, 13 Drawing Figures

SUCTION INJECTOR

CROSS-REFERENCE TO RELATED APPLICATIONS

This application is a continuation-in-part of my co-pending patent application Ser. No. 93,615, filed Nov. 9, 1979 and matured into U.S. Pat. No. 4,284,077 and which is a divisional application under 37 CFR 1.60 of prior patent application Ser. No. 933,136 filed Aug. 14, 1978 which is now abandoned and is in turn a continuation-in-part of the patent application Ser. No. 793,951, filed May 5, 1977, and matured into U.S. Pat. No. 4,114,691 and, which in turn is a continuation-in-part of my application Ser. No. 634,741, filed Nov. 21, 1975, now abandoned, and the entire disclosure of which is herewith incorporated by reference. This application is also related to my copending patent applications Ser. No. 618,686 filed Dec. 21, 1975, now abandoned Ser. No. 634,742, filed Nov. 21, 1975, now abandoned and Ser. No. 639,685, filed Dec. 8, 1975, now abandoned all of whose disclosures are also herewith incorporated by reference.

BACKGROUND OF THE INVENTION

The invention relates generally to the medicine technology, and more particularly, it relates to the injection therapy or subcutaneous extration of samples.

Devices, which drive injection cannulas into the body by sucking first the skin against the cannula tip are known from prior art. With the suction injection bones, vessels and nerves are not touched and the medicine inflow into the tissue is facilitated and pain is avoided.

The known devices of this type however have the disadvantages that they are relatively bulky and are difficult to be operated by the patient himself. Small suction injectors using an exchangeable syringe have the difficulty to locate exactly the point on patients' skin where the puncture is to be made and the charging of the syringe with the medicine is frequently a cumbersome operation.

Furthermore, the prior art suction injectors do not ensure a relatively quick release of the cannula tip from human skin which is rather inconvenient and may be painful for a patient.

SUMMARY OF THE INVENTION

It is therefore an object of the invention to overcome the disadvantages of the prior art suction injectors.

Another object of the invention is to provide an improved suction injector which can be easily manipulated by one hand only and may be easily released from the human skin after the injection.

Still another object of the invention is to provide a suction injector in which the cannulas can be easily exchanged.

A further object of the invention is to perform the injection with the assistance of negative pressure accumulated in the suction cup so that the skin to be treated will be lifted by this negative pressure towards the cannula tip. The application of the negative pressure permits one to avoid pressure of the suction cup to bones, nerves and blood vessels since vacuum produced over the skin forces the skin into the cannula in the syringe.

These and other objects of the invention are attained by a suction injector, particularly for use with hypodermic injections, comprising a container filled with a liquid medicine; a piston arranged for movement in said container; an exchangeable cannula operatively connected to said container; a suction cup having an outer cylindrical portion defining an outer chamber and an inner cylindrical portion defining an inner chamber, said inner chamber having a surface to be positioned over human skin to be treated, said inner portion having an aperture for receiving said cannula through which the liquid medicine is discharged upon the movement of said piston and at negative pressure which is accumulated in said outer chamber during fabrication, and means for preventing communication of the negative pressure in said outer chamber to said inner chamber until said inner chamber is in pressure contact with the skin.

A membrane closing the inner portion may define the surface over the human skin, the communication preventing means supporting said membrane whereby said membrane together with the skin to be treated is lifted by the negative pressure towards said cannula.

The communication means may include a substantially tubular member associated with said inner chamber and provided with a number of flexible projections, said membrane closing said tubular member.

The tubular member is sealed from the outer chamber in the suction cup when said cannula is in an idle condition, the flexible projections being adapted to break the seal between said outer chamber and said tubular member when said membrane is lifted towards the cannula.

The inner cylindrical portion may be formed with a relatively thin radial extension, said flexible projections being adapted to penetrate through said radial extension to break said seal when said tubular member is lifted towards said cannula.

The injector may be provided with a guiding device including a cylindrical chamber having an outer wall defining said suction cup and a guiding bar formed with a guiding groove for supporting the cannula.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompany drawing.

BRIEF DESCRIPTION OF THE DRAWING

FIG. 1a is a sectional side view of a modification of the syringe cylinder in the injector of FIG. 1;

FIG. 1b is still another modification of the suction injector of FIG. 1;

DETAILED DESCRIPTION OF THE PREFERRED EMBODIMENTS

Figure 1:
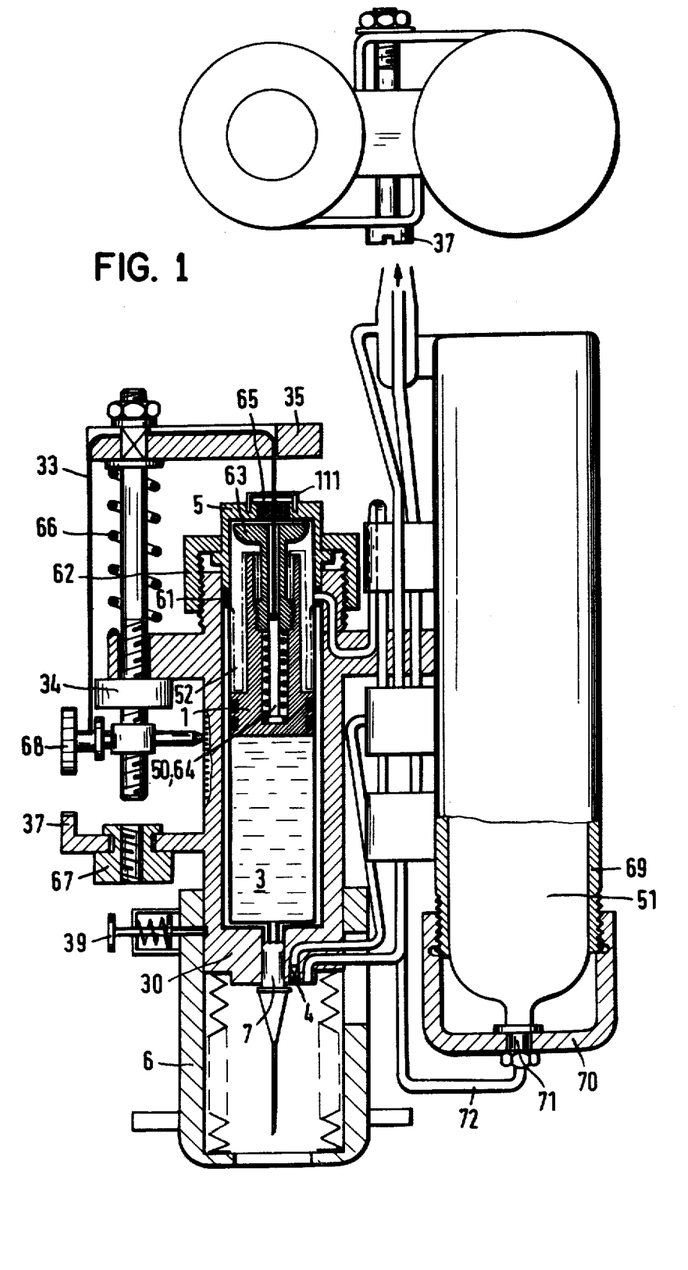
FIG. 1 is a sectional side view of one embodiment of a suction injector according to this invention.
Figures 3, 3A, 3B:
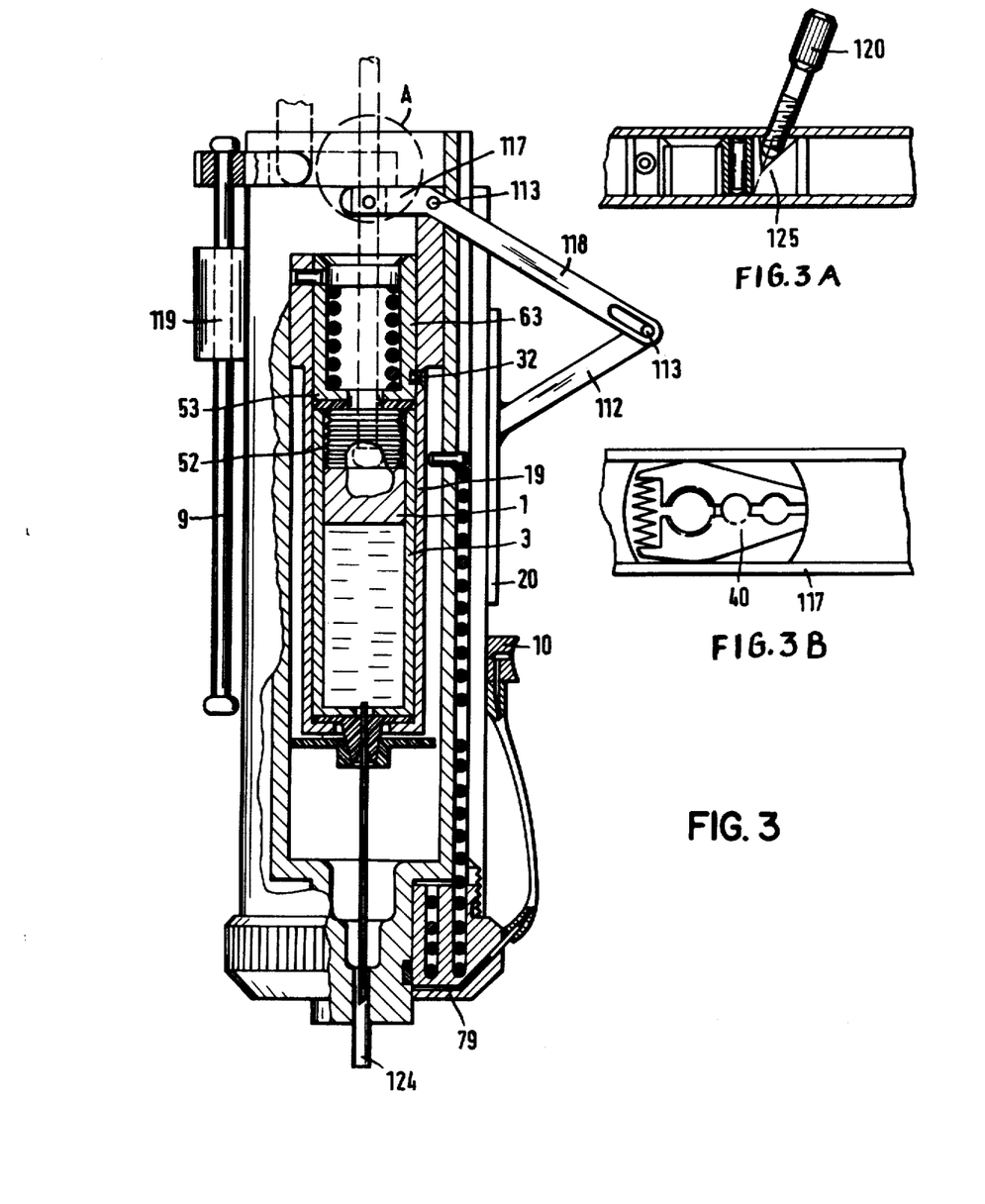
FIGS. 3, 3A and 3B illustrate still another modification of the suction injector.
Figure 3:
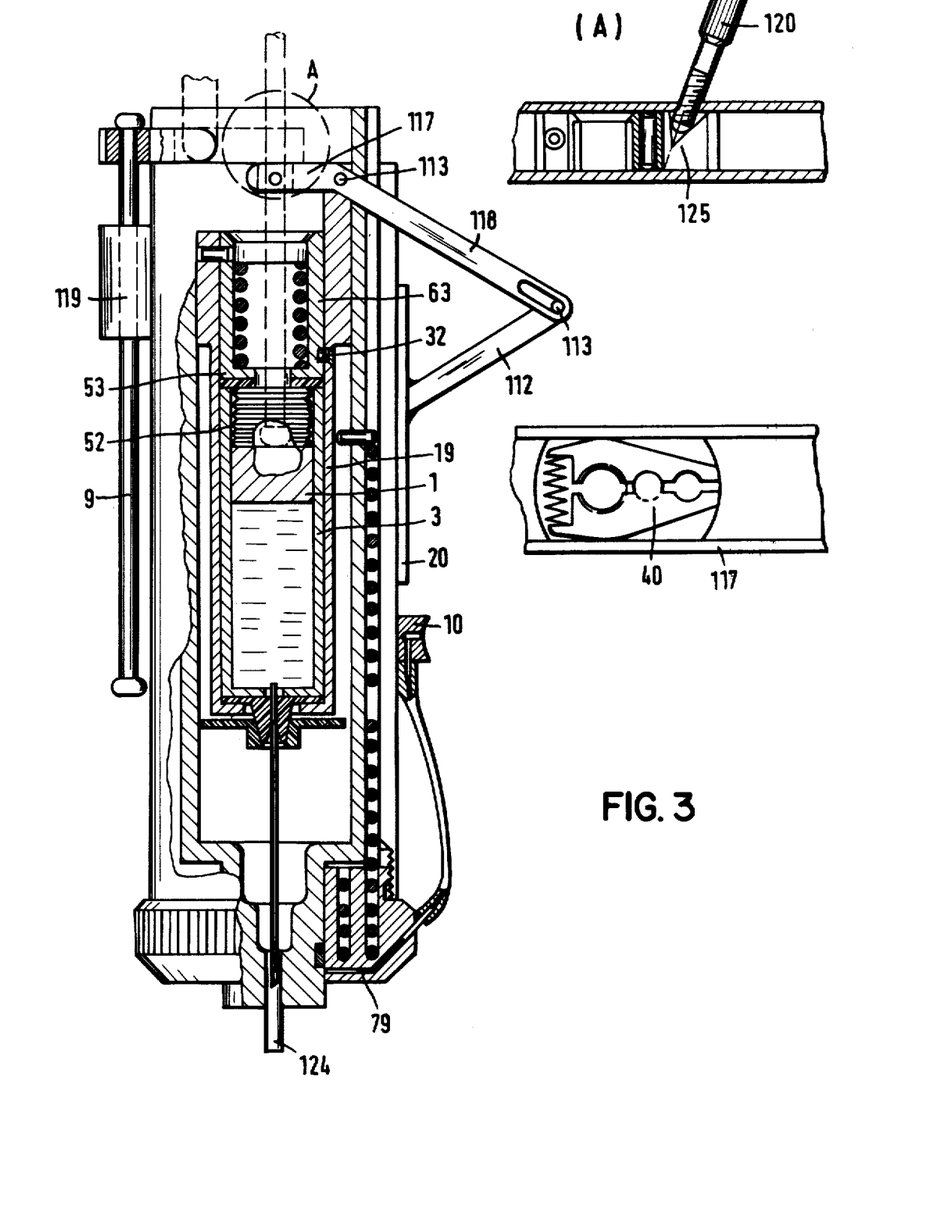

FIG. 1 shows the first example of the invention in a vertical section. The head piece 1 consists of a beaker 2, in which the syringe-cylinder 3 is inserted, as well as the suction cup 4 for sucking in the skin, and the flange 5 for the handle piece. The handle piece may be made of a relatively elastic material. An air tube 7 leads from the opening 8 of the syringe cylinder to the skin which has been sucked in. In the middle of the flange there is a cylindrical hole 9, in which a conical stopper 10 moves with friction. The stopper is pulled into the basket piece 15 by the suction between the handle cylinder 11 and the handle piston 12 against the pressure of the spring 14, which may be regulated by the screw-on cap 13. This permits air to enter through the cylindrical hole 9. The pumping function of the handle cylinder and the handle piston is guaranteed by a seal 16. The handle cylinder 11 contains a hole 17, which is sealed with a rubber ring 18. When the handle piston 12 is pulled back, the resulting suction causes that part of the rubber ring 18 which is over the hole 17 to curve inwards and activates the catch 19, which returns to its original position after the pressure has been reduced. FIG. 3 shows a better solution of a transfer of the power of the catch 38 for the piston behind the vacuum over the lever 21, which through the suction is lowered onto the valve plate 39. The remaining suction and the tension spring 23 return the handle piston 12 to the original position. At the same time a rod 24 placed in the center of the handle piston pushes the stopper 10 into the cylindrical hole of the flange. The neck of the handle piece offers mobility through the elasticity of the material. A loop 6a on the handle cylinder, which could be hooked onto a door handle, and a handle on the end of the handle piston 12 facilitates the use of the apparatus for weak persons. The depth of the penetration of the cannula can be reduced through the elastic rings 20. The extent of the arcing of the rubber ring 18 into the handle cylinder can be regulated by a nut in the handle cylinder after the removal of the rubber ring.

The syringe cylinder 3 consists of an outer cylinder with a bottom piece 25, which besides the opening 8 has several chambers 26 to balance the air pressure. The cannula 28 is on the end of the inner cylinder 27, which is attached to the outer cylinder but movable. In rest position, the point of the cannular reaches into the opening 8 of the outer cylinder. The liquid stream is forced through cannula into the inner cylinder by the pressure of the filler-neck cone in a conical hole 29 against the seal ring 30, thus raising the inner piston 31 and forcing air through the porous membrane 32. A suction effect draws the outer piston 33 which is on the opposite end of the outer cylinder from the bottom piece 25, which is stopped by nobs 34 on the inner wall of the outer cylinder or by friction of an insulating outer foil 35. As the outer piston is being pulled by the suction, it pushes with its rod or filter plate the inner membrane 32, thus moving the inner piston back. The inner cylinder is kept in a straight position by means of spikes 37 or fins. The impact of the inner piston breaks the inner membrane, the rod 36 pushes the inner piston, through which the contents are emptied. The seal of the bottom part of the outer cylinder is effected through germ-protecting membrane.

In FIG. 1a a variation of the syringe cylinder is shown, in which the inner cylinder and the cannula are replaceable. A shell 42 to which the seal ring 30a and air chambers 26 are attached functions at its further end as a protective capsule 40 which encloses the inner cylinder and cannula. In place of the inner piston the end of the rod 32 is transformed into an inner piston itself, so that by lowering of the outer piston with the handle 33a the elastic membrane 32 over the inner cylinder is pushed in. The conical shape of the inner cylinder balances the differences in friction caused by the thinning out of the membrane brought about by the lowering of the rod. The shell is stopped by catches in the bottom part of the outer cylinder and is released again by the use of a ring fastener or by cushioning pegs through the beaker. A nob barrier between the inner cylinder 44 and the protective shell 27a prevent them from being shoved against one another. The fins 43 for the stabilization of the movement of the inner cylinder are attached to the inner wall of the outer cylinder.

In FIG. 1b, a modification of facilitated vacuum production is shown by means of a reduction pump. When the piston is pulled, the check valve 45 closes, while the check valve 46 is opened towards the larger cylinder space. An under-pressure is produced, so low, that the security valve 47 is opened, while the incoming air causes a whitling sound. The transfer of the under-pressure to the head piece occurs through the valve 48, which is opened over the lever 50 when the guiding cylinder 49 around the suction cup is activated.

Figure 2:
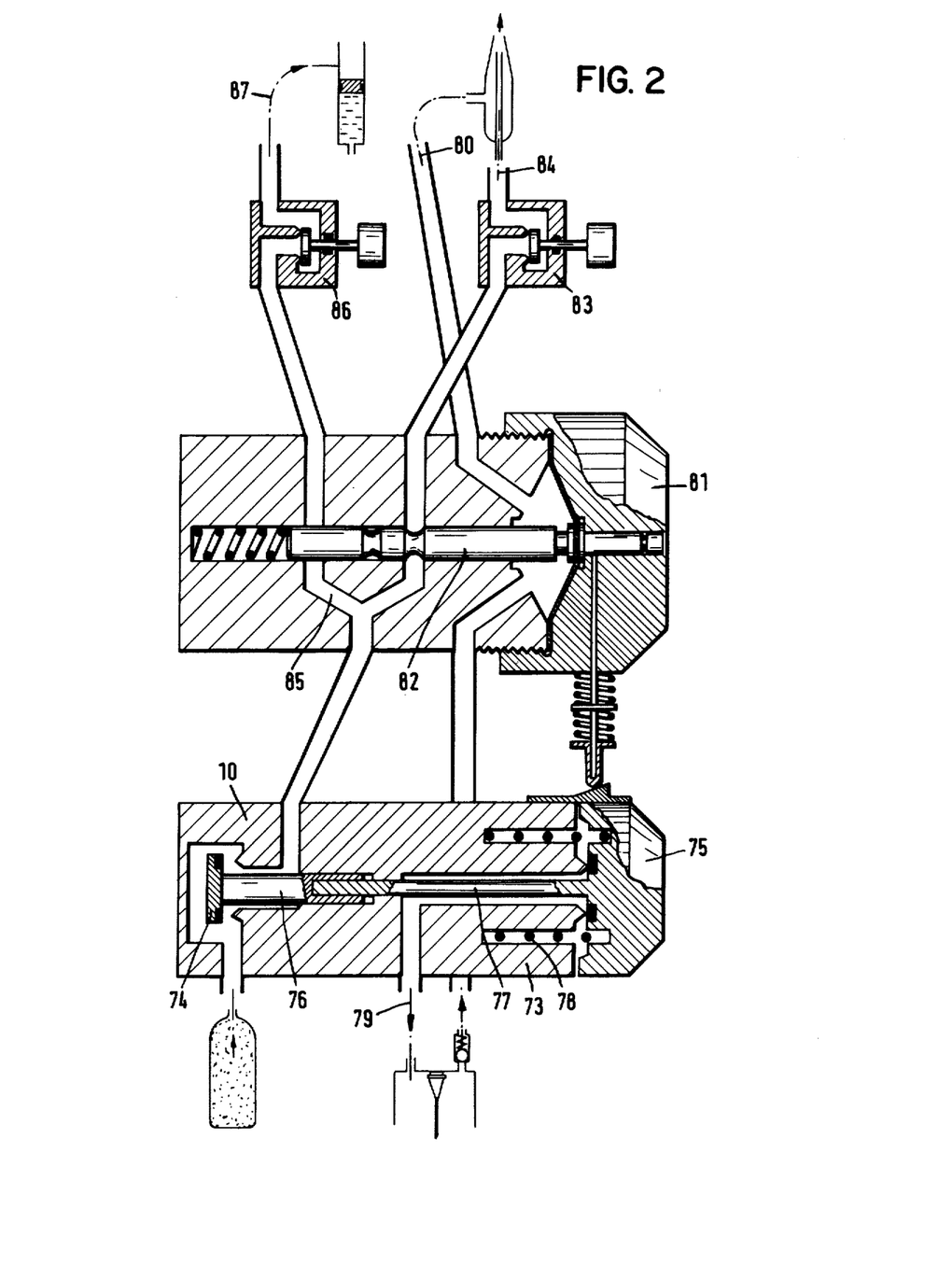
FIG. 2 is a sectional side view of a suction injector in which a syringe cylinder is replaced by an elastic bag for receiving the liquid medicine.

In FIG. 2 the syringe cylinder is replaced by a cannula with an elastic bag which surrounds the blunt end of the cannula and has ring-formed plastic seals. A cannula capsule surrounds the shaft and contains a guiding shell 61. The handle piece in the second example is changed as indicated in the Figure. The cannula-leading-cylinder 51 leads over the piston 52 and it leads over another piston 53 which is firmly connected to a holding bridge 54. From its edge the cannula-leading-cylinder 51 leads an elastic membrane to the edge of a funnel insulating ring 55. The inside end is formed by a central seal 56, which over a pressure valve 57 is connected with the inner piston space. Pressure in this space can be reduced by a hand switch 58. The cannulaleading-cylinder 51 together with the seal ring can be raised to lead in the cannula 28. The cannula 28 is conically formed. Adjusting screws on the catch 59 permit a regulation of the depth of penetration into the skin. The bottom cone 60 contains chambers 26 of the equalization of air pressure, a cushioning movable in guiding shell 61, and a ring to guide the cannula 28. The switch 62 activates the blocking switch 63, which frees the motion of the piston 52, so that the contents of the bag are emptied. The cannulaleading-cylinder moves backwards after the suction switch 64 is freed by movement against the piston as well as through simultaneous suction under the membrane 65 in the direction of the sides of the funnel 66. The pressure in the inner piston space 67 can be increased by a hand switch 58 before the injection. The air compression occurs in the handle piece through the pushing together of the handle cylinder 11 and the handle piston 12, and by this the check valve 68 is closed in the cylindrical hole 9 and the check valve 69 is opened into the space in the holding bridge. The suction process occurs in the same manner as described in FIG. 1. In a variation, which relates to intramuscular injections, the cannula-leading-cylinder 51 is now a bit higher 70 and held firm by suction switch 64. The funnel insulation ring 55 is fastened by a clamp to the funnel. The switch 62 is drawn away and the blocking switch 63 is put out of action. The suction which is created activates the suction switch 57, which frees piston 52. If the point of the cannula has penetrated a blood vessel, the bag fills and prevents a suction effect on the suction switch 57. The dose mechanisms for all of the mechanisms which are described here correspond to those technically known.

Figure 4:
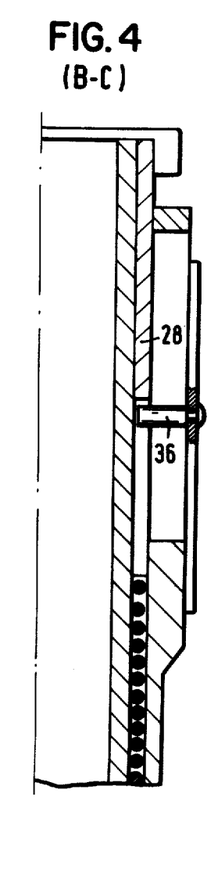
FIG. 4 is a sectional view of another embodiment of the suction injector having a dosing mechanism.

FIG. 4 shows an example in which the characteristics and advantages of the mechanism presented in FIGS. 1 and 2 are combined and in which a dosing is possible inside of the mechanism. The dosing occurs in the space between the rod 36 and the cannula neck 88, in which the bag can spread out, depending on how wide the threaded tube 89 with a blocking plate 90 resting on it is screwed back into the inner cylinder 27. The turning on its axis of the inner cylinder is prevented by the impact of the nobs 91 on the leading fins of the outer cylinder; the transfer of the turning from the outer piston to the rod and threaded tube occurs by means of guide grooves and channel 92. The clamps 93, which are attached to the outer piston, support the inner cylinder 27 on the nobs, until they are struck by the fork segments 94 on the guiding fins, which let the nobs by, while spreading the clamps away from the nobs. Now the movement of the rod causes the cannula bag to be emptied. The downward movement of the outer piston is delayed by friction, so that the suction on the skin lasts longer, for the purpose of leassening the sensitivity to pain.

Figure 5:
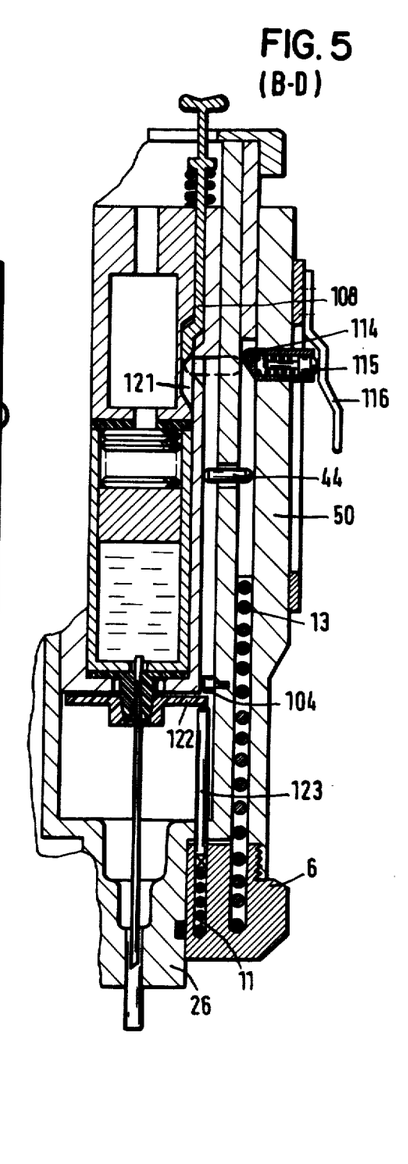
FIG. 5 shows in partly sectional view a further embodiment of a suction injector having means for filling the syringe through the cannula.

FIG. 5 shows an example without handle, consisting of only a cylinder, which has a double wall in order to create a reserve vacuum. The filling takes place by means of a cannula through the outer foil and the inner piston 31. Thus the inner piston moves back as a result of the pressure from the liquid against the spring 95, the check valve 96 being sealed on the syringe cone. Pressure on the hand button frees at first the pegs 97 on the suction cup. When the hand buttons move back cushioned by springs, the pegs 98 into the outer piston are pulled. The opening of the check valve 96 is ensured by the snapping shut of a kind of snap fastener 99. On the end of the syringe cylinder or the suction cup, there is a changeable membrane 100, which is at least on the inside sterile, and which when in use draws back together with the skin and prevents a direct contact between the skin and the apparatus and preserves sterility before use. A suction inlet 101 is prepared.

Figure 6:
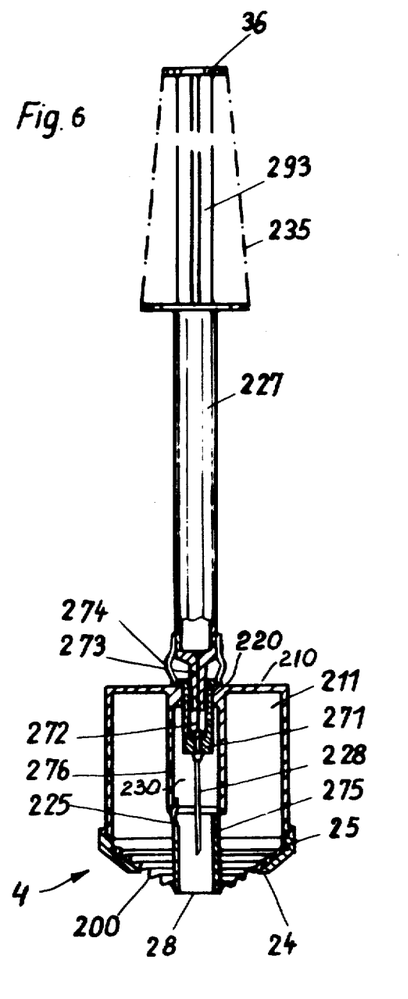
FIG. 6 illustrates a partially sectional view of still another embodiment of a suction injector having means for blocking the negative pressure into the cannula supporting tube according to the invention.

FIG. 6 illustrates a suction injector including a suction cup 4 for sucking in the skin and a medicine containing cylinder 227. The suction cup includes an outer substantially cylindrical portion 210 and an inner also substantially cylindrical portion 276 defining an inner chamber 230 and having an opening 220 to receive a supporting element 271 of the cannula 228. The cannula tip is surrounded by a supporting tube 275 which is provided at its periphery at the upper end thereof with three flexible tongues 225 which are supported on the inner surface of the inner portion 276. An outer chamber 211 is formed between the outer walls of the suction cup 4 and the inner cylindrical portion 276. The upper end of the tube 275 is sealingly connected to the lower end of the inner portion 275 so that negative pressure provided and accumulated in the outer chamber 211 in fabrication is maintained when the syringe is in the idle condition. The supporting tube 275 is closed at the lower end thereof with a membrane 28. A folded bellows 200 extends between the supporting tube 275 and the lower edge of the outer chamber 211. The upper portion of the bellows 200 is surrounded by a ring 25 which also encircles the lower edge of the suction cup or suction bell 4.

The cylinder 227 is terminated with a downwardly projecting element 273 of the cannula which in turn is slidably arranged in a conical hole provided in the supporting element 271. The element 273 is surrounded by a socket 274 and arranged to receive a valve pin 272 which extends downwardly towards the outlet of the element 273. A piston 36 is located within the cylinder 227. A predetermined amount of the liquid medicine to be injected under the surface of the site selected for injection is located under the piston. The piston is surrounded by a slotted supporting shell 293 and closed by a protecting membrane 235. In practice the protecting membrane may be removed from the supporting shell 293.

Figure 7:
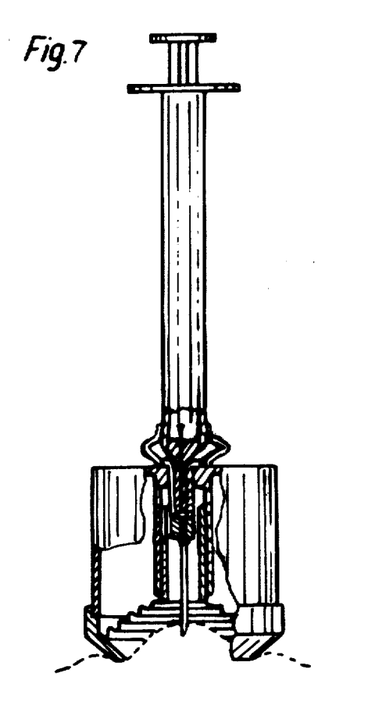
FIG. 7 is a view showing the suction injector of FIG. 6 in operation.

Before use the device is removed from the sterile package and positioned over human skin so that the membrane 28 contacts the surface of the skin. By action of the piston 36 pressure is exerted within the inner chamber 230 whereby the resistance of the flexible tongues 225 contacting the inner surface of the inner portion 275 is overcome. This results in the sliding movement of the supporting tube 275 inward of the inner portion 276, which movement is now assisted by vacuum accumulated in the chamber 211 which is now communicated with the inner chamber 230 since the seal between the two chambers is broken by the tongues 225 due to their slidable movement in the upward direction. Due to this slidable movement the folded bellows 200 together with human skin will be drawn up whereby the cannula tip will penetrate the membrane 28 and then the human skin to be treated. At this time by lowering of the projecting element 273 the valve pin 272 will slide upwards and the medicine to be applied to the skin will be released. The injection is performed by usual lowering of the piston 36 in a conventional fashion. The position of human skin immediately before the injection is shown by a dotted line in FIG. 7. After the completion of the injection the device is removed from the skin. As seen in FIG. 7 the skin is lifted under negative pressure and contacts with the folded bellows 220 which are inwardly pressed due to the upward movement of the tube 275.

Figure 8:
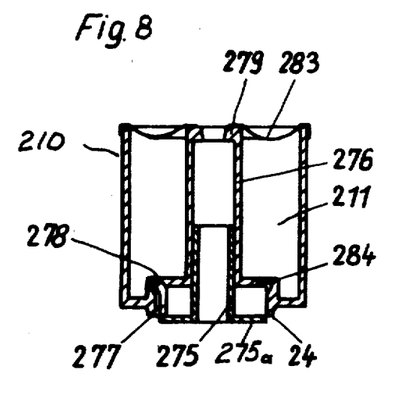
FIG. 8 is a partially sectional view of a further embodiment of a suction injector with negative pressure blocking means.

FIG. 8 illustrates a modification of the suction cap shown in FIGS. 5 and 6. According to this embodiment, the outer chamber 21 is provided with a central conical opening 279 adapted to receive the projecting portion of the cannula (not illustrated herein). At the lower portion thereof the inner portion 276 of the suction bell 276 is formed with a substantially cylindrical downwardly projecting strip-like rim 24 and a relatively thin portion 284. The supporting tube 275 which is adapted to slide inwardly upwardly of the tube 276 is provided with a ring-shaped bottom portion 275a. This bottom portion has three sectorlike arms 277 (also shown in FIG. 9) equally spaced from one another in a circumferential direction which are located at the periphery of the bottom portion 275a and extend upwardly from the surface thereof. The arms 277 have slightly outwardly curved ends which may easily penetrate the thinned portion or extension 284 of the tube 276 and break the seal between the outer chamber 211 and inner chamber 230 in a fashion similar to that described for FIG. 6. The thinned portion 284 may be replaced by strips which merge into the walls of the suction bell. In evacuated position the outer chamber 211 is closed with membrane 283.

Figure 9:
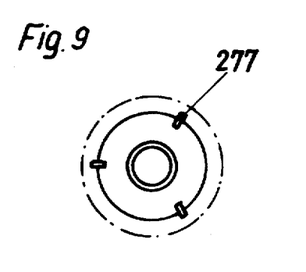
FIG. 9 is a top plan view of a skin contacting ring shown in the FIG. 8 in assembly.

FIG. 9 shows a plan view of the supporting tube 275 having arms 277 wherein an outer dotted line illustrates the outer ends of the arms 277 in their upward position. The supporting tube with arms may be made of polyvinylchloride whereas the remaining parts of the device may be formed of polystyrene.

In practice the cannula which is adjusted to a filled syringe may be inserted into the opening 279 in a manner as shown in FIGS. 6 and 7.

When the device is removed from a sterile container and the supporting tube 275 is placed over the skin to be treated the ends of the arms 277 of the bottom portion 275a penetrate the thinned portion 284 due to the movement of the tube 275 upward within the inner portion 276. Due to resulting openings in the portion 284 the inner chamber 230 will communicate with the outer chamber 211 accumulating negative pressure whereby the rim 24 and the human skin tightly associated therewith will be lifted by said negative pressure towards the cannula and the liquid medicine will be discharged from the tip of the cannula by pressing the spraying piston in a conventional mode.

Figure 10:
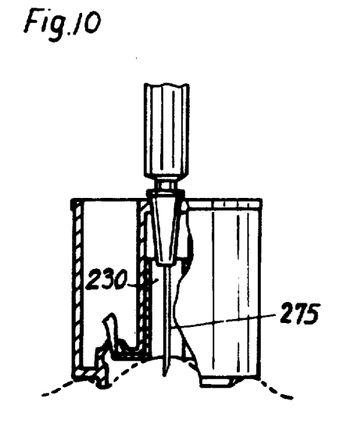
FIG. 10 is a view illustrating the suction injector of FIG. 8 in operation.

FIG. 10 illustrates an axial section of the suction cup immediately before or after the injection. The position of the human skin is illustrated by a dotted line.

Figure 11:
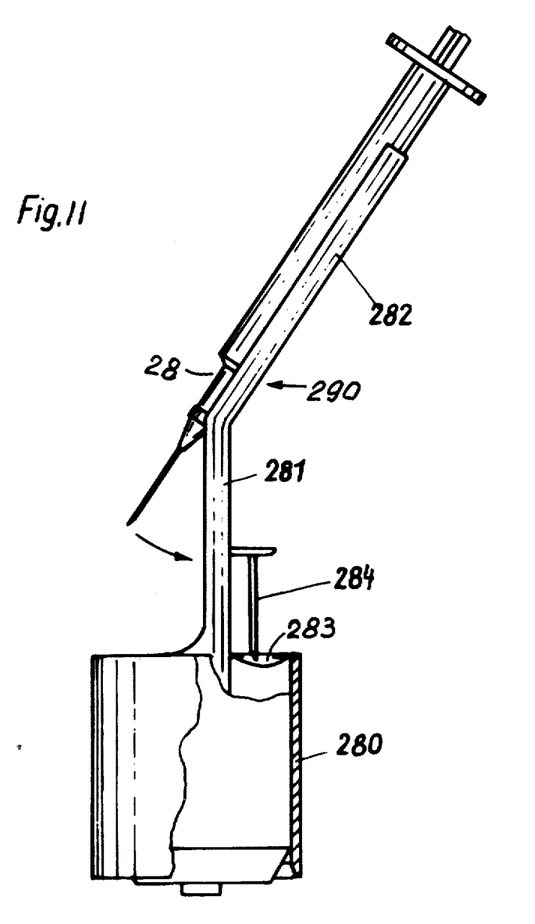
FIG. 11 is a view, partially in section, of a still further embodiment of the suction injector.

FIG. 11 shows an auxiliary device for guiding the cannula 28 shown in FIGS. 6-10. This device includes a cylindrical body 280 which is opened from the bottom and provided with a guiding bar 290 including a straight portion 281 and a sloped portion 282, both formed with a guiding channel for supporting of the preliminarily filled cannula. The cannula 28 slides in the sloped portion 282 until it tips into the straight portion 281 along which it slides further into the central conical opening 279. The suction injector may be placed into the cylindrical body 280 of the auxiliary device which may be positioned over the surface of the site selected for injection and the injection then may be performed as described above.

Additionally, the auxiliary device may be provided with an elastic angle 284 which perforates into the ring-shaped membrane 283 so that ambient air may flow into the suction bell. The skin is thus pulled back out of the cannula and the injector may be lifted and removed from the auxiliary device which may be used repeatedly.

It will be understood that each of the elements described above, or two or more together, may also find a useful application in other types of suction injectors differing from the types described above.

While the invention has been illustrated and described as embodied in a suction injector, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A suction injector, particularly for use with hypodermic injections, comprising a container filled with a liquid medicine; a piston arranged for movement in said container; a cannula operatively connected to said container; a suction cup having an outer cylindrical portion defining an outer chamber and an inner cylindrical portion defining an inner chamber, said inner chamber having a surface to be positioned over human skin to be treated, said inner portion having an aperture for receiving said cannula through which the liquid medicine is discharged upon the movement of said piston and at negative pressure which is accumulated in said outer chamber during fabrication; and means for preventing communication of the negative pressure in said outer chamber to said inner chamber until said inner chamber is in pressure contact with the skin.

2. The injector of claim 1, wherein said outer chamber is defined between said outer portion and said inner portion.

3. The injector of claim 2, further including a membrane defining said surface to be positioned over human skin, said communication preventing means supporting said membrane whereby said membrane together with the skin to be treated is lifted by said negative pressure towards said cannula.

4. The injector of claim 3, wherein said communication means includes a substantially tubular member associated with said inner chamber and provided with a number of flexible projections, said membrane closing said tubular member.

5. The injector of claim 4, wherein said tubular member is sealed from said outer chamber when said cannula is an idle condition, said flexible projections being adapted to break the seal between said outer chamber and said tubular member when said membrane is lifted towards said cannula.

6. The injector of claim 5, further including bellows interconnected between said outer portion and said tubular member.

7. The injector of claim 5, wherein said tubular member includes a tube and a bottom portion, said flexible projections being formed on said bottom portion.

8. The injector of claim 7, wherein said inner cylindrical portion is formed with a relatively thin radial extension, said flexible projections being adapted to penetrate said radial extension to break said seal when said tubular member is lifted towards said cannula.

9. The injector of claim 8, wherein said outer chamber is sealingly closed at the upper and the lower ends thereof by ring-shaped seals.

10. The injector of claim 1, wherein said cannula includes a valve means for discharging the liquid medicine therefrom.

11. The injector of claim 10, further including a diaphragm at least partially closing said outer chamber from above.

12. The injector of claim 1, further including a device for guiding said cannula for the injection.

13. The injector of claim 12, wherein said guiding device includes a cylindrical member having an outer wall defining said suction cup and a guiding bar formed with a guiding groove for supporting said cannula before insertion into said cup.

14. The injector of claim 13, wherein said guiding bar includes a straight portion communicating with said outer chamber and a sloped portion remote from said outer chamber, said cannula being adapted to slide along said guiding groove into said opening in said suction cup.

* * * * *